United States Patent [19]

Finnan et al.

[11] Patent Number: 4,830,859
[45] Date of Patent: May 16, 1989

[54] PROCESS FOR LUBRICATING WATER-SOLUBLE VITAMIN POWDERS

[75] Inventors: Jeffrey L. Finnan, Southgate; Rudolph E. Lisa, Grosse Ile; Joseph T. Wisniach, Riverview, all of Mich.

[73] Assignee: BASF Corporation, Parsippany, N.J.

[21] Appl. No.: 103,097

[22] Filed: Sep. 30, 1987

Related U.S. Application Data

[63] Continuation of Ser. No. 724,250, Apr. 17, 1985, abandoned.

[51] Int. Cl.$^4$ .......................... A61K 9/20; A61K 9/14; A61K 9/16; A61K 31/34
[52] U.S. Cl. .................... 424/465; 424/489; 424/494; 424/495; 514/474; 514/960
[58] Field of Search .................. 424/38; 514/474, 960

[56] References Cited

U.S. PATENT DOCUMENTS

| | | | |
|---|---|---|---|
| 2,805,977 | 9/1957 | Robinson et al. | 424/38 |
| 2,840,504 | 6/1958 | Vierling | 424/38 |
| 3,119,742 | 1/1964 | Heimlich et al. | 424/38 |
| 3,145,146 | 8/1964 | Liebermann et al. | 424/38 |
| 3,247,065 | 4/1966 | Koff | 424/38 |
| 3,341,415 | 9/1967 | Scott | 514/960 |
| 3,725,556 | 4/1973 | Hanssen et al. | 514/960 |
| 4,203,997 | 5/1980 | Küppers et al. | 514/960 |
| 4,533,674 | 8/1985 | Schmidt et al. | 514/474 |

*Primary Examiner*—Douglas W. Robinson
*Assistant Examiner*—Joseph A. Lipovsky
*Attorney, Agent, or Firm*—Rupert B. Hurley, Jr.

[57] ABSTRACT

The subject invention relates to a process for preparing lubricated water-soluble vitamin powders. The water-soluble vitamin powders are lubricated by combining them with a lubricant at a temperature sufficient to melt the lubricant. The powders are directly compressible into tablets and are resistant to demixing.

13 Claims, No Drawings

PROCESS FOR LUBRICATING WATER-SOLUBLE VITAMIN POWDERS

This is a continuation, of application Ser. No. 724,250, filed Apr. 17, 1985, now abandoned.

BACKGROUND OF THE INVENTION
1. Field of the Invention

This invention relates to a process for preparing a lubricated water-soluble vitamin powder. Particularly useful water-soluble vitamins used to make the powder are ascorbic acid, sodium ascorbate, and calcium ascorbate. The lubricated powder is directly compressible into tablets and is resistant to demixing.

2. Description of the Prior Art

It is known to prepare water-soluble vitamin powdersbby spray drying a water-soluble vitamin with various excipients such as a binder and an adsorbent. The prior art also teaches that a lubricant needed for tableting can be manually blended with the powder. See for example U.S. Pat. No. 3,293,132.

The prior art, however, does not teach that the lubricant is combined with the water-soluble vitamin powder at a temperature which is sufficient to melt the lubricant. This modification provides powders which are resistant to demixing. Demixing is undesirable because it results in a non-uniform distribution of the lubricant in the powder. Moreover, the prior art does not teach that a lubricated powder can be prepared by a continuous process which is the case when a powder is prepared by spray drying and then passed through a continuously operated fluidized bed at a temperature sufficient to melt the lubricant.

SUMMARY OF THE INVENTION

The subject invention relates to a process for preparing a lubricated water-soluble vitamin powder comprising
combining said powder with an effective amount of a lubricant at a temperature sufficient to melt the lubricant.

Particularly useful as the water-soluble vitamins are ascorbic acid, sodium ascorbate, and calcium ascorbate.

The lubricated powder is directly compressible into tablets and is resistant to demixing. Moreover, if the water-soluble vitamin powder is prepared by spray drying, the process can be practiced as a continuous process by passing it through a fluidized bed dryer where it is combined with the lubricant at a temperature sufficient to melt the lubricant.

DESCRIPTION OF THE PREFERRED EMBODIMENT

The tabletable water-soluble vitamin powders which are lubricated by the process herein can be prepared in any conventional manner such as wet granulation, slugging, fluid bed granulation, etc. However, it has been found that preparing them by spray drying is advantageous because the spray dried powder can be directed to a fluidized bed dryer in a continuous process where the powder will be lubricated. If the powder is prepared by spray drying, an aqueous slurry of the water-soluble vitamin, binder, and optionally an adsorbent are spray dried according to conventional methods.

Specific examples of water-soluble vitamins include ascorbic acid, sodium ascorbate, calcium ascorbate, niacin, riboflavin, pyridoxine, calcium d-pantothenate, thiamine hydrochloride, thiamine nitrate, pantothenic acid, folic acid, and biotin. Of more interest, however, are ascorbic acid, sodium ascorbate, and calcium ascorbate. Natural sources of these water-soluble vitamins, such as rosehips, may also be used, preferably in minor amounts.

Typical binders (for example, see U.S. Pat. No. 3,293,132 at column 3, lines 29–54) that can be used include proteins such as gelatin, water-soluble derivatives of casein, e.g., sodium caseinate, and the like; water-soluble gums such as gum acacia, gum karaya, gum ghatti, tragacanth, and the like; cellulose, and water-soluble derivatives of cellulose such as methylcellulose, hydroxyethyl cellulose, sodium carboxymethylcellulose, and the like. For this purpose, use may furthermore be made of certain polyvinyl resins such as, for example, polyvinyl alcohol, polyvinyl pyrrolidine and the like. Preferably used with ascorbic acid, sodium ascorbate, and calcium ascorbate are micro-crystalline cellulose, and mixtures of microcrystalline cellulose and hydroxypropylmethylcellulose.

To prepare the aqueous slurry, the water-soluble vitamin and binder are added to enough water to make a finished feed slurry having about 10 to 90 percent solids by weight, and, preferably, about 50 to 75 percent by weight solids.

The aqueous slurry containing the water-soluble vitamin and binder is preferably spray dried in the presence of an adsorbent such as those disclosed in U.S. Pat. No. 3,914,430 at column 3, lines 43–68, which is hereby incorporated by reference. Preferably used as the adsorbent is silicon dioxide, particularly silicon dioxide having a particle size of from 0.1 to 10.0 microns.

Additional excipients may also be used to prepare the water-soluble powders. Although not used in a preferred basis because of nutritional factors, the subject powders may also contain carboxyhydrates such as sugars including lactose, sucrose, maltose, glucose, mannose, fructose, arabinose, and the like; and closely related polyhydric alcohols containing from 4 to 6 hydroxyl radicals such as mannitol, dulcitol, sorbitol, and the like.

Any suitable spray dryer may be used to prepare the water-soluble vitamin powders such as a vertical spray dryer equipped with a means of making droplets, such as rotary atomizer operated between 10,000 and 35,000 rpm, preferably 18,000 to 25,000 rpm for a small dryer or suitable atomizer nozzles (such as high pressure, two- and three-fluid). The inlet temperature is maintained at 170° C. to 230° C. and the outlet temperature is a function of the inlet temperature and flow rate, generally between 90° C. to 100° C. The aqueous slurry of water-soluble vitamin and microcrystalline cellulose is then spray dried to form a free-flowing, nonagglomerated powder.

The water-soluble vitamin powder which results from the spray drying process or from other conventional methods is then mixed with a lubricant at a temperature sufficient to melt the lubricant, generally at least 50° C. Preferably used as the lubricant are stearic acid, magnesium stearate and mixtures thereof. However, other stearic acid salts may be used such as calcium stearate. Also, there can be used wax-like materials, for instance, wax-like saturated fatty acids, wax-like mixtures containing two or more saturated fatty acids or wax-like hydrogenated glyceride, in admixture with a metallic stearate and/or titanium dioxide such as are disclosed in U.S. Pat. No. 3,396,226 (column 3, lines 29–55) which is hereby incorporated by reference.

Although any mixing device (such as a jacketed v-blender, jacketed ribbon blender, batch fluid bed, etc.) to which heat sufficient to melt the lubricant can be applied, can be used, it has been found that a continuous fluidized bed dryer is particularly useful for this purpose. Using a continuous fluidized bed dryer, such as a vibrating bed dryer, enables one to practice this invention as a continuous process if the water-soluble vitamin powder is prepared by spray drying. According to this embodiment of the invention, the spray dried water-soluble vitamin powder is directly channeled to a fluidized bed dryer where it is mixed with the lubricant at a temperature sufficient to melt the lubricant. This embodiment of the invention provides an effective, uniform method of mixing and heating, and will result in a uniform product which is resistant to demixing.

The components described herein are used in effective amounts. Those skilled in the art can determine what amounts are to be used based upon their own experience and the examples set forth herein. However, when ascorbic acid, sodium ascorbate, and calcium ascorbate are used as the water-soluble vitamin, the components described herein preferably are added in amounts such that the final powder formed will contain at least 80 (preferably at least 90) percent by weight of the water-soluble vitamin, less than 15 percent by weight of binder, 0.2 to 2 percent by weight of adsorbent, and 0.2 to 5 percent by weight of the lubricant and less than 3 percent of other excipients. Although these amounts may also be effective for other water-soluble vitamins, those skilled in the art may discover better proportions with them and for specific purposes.

Tablets from the lubricated powder are made by conventional methods. Useful tableting aids are disclosed in *Pharmaceutical Technology*, July, 1980, pages 27–35, and 62.

The examples which follow will provide more details regarding how to practice the invention. In the examples, unless otherwise stated, all parts are by weight and all temperatures are in degrees centigrade.

EXAMPLE 1

This example illustrates the preparation of a water-soluble vitamin powder by spray drying and mixing the lubricant and powder in a fluidized bed dryer.

A suspension was made in a stainless steel jacketed tank equipped with an agitator by adding hot water to 21 parts of hydroxypropylmethylcellulose such that the resulting suspension had a solids weight of 7.1 percent by weight. The suspension was heated to about 80° C. and then cold water was added in an amount such that the suspension had 2.5 percent solids. Then 933 parts of ascorbic acid and 46 parts of microcrystalline cellulose were added.

The resulting slurry along with silica at a rate of 25 lbs/hr was sprayed into a 24 foot diameter vertical spray dryer through four high pressure nozzles at about 2,000 psig pressure.

| Component | Percent by Weight Based on the Weight of the Dry Powder |
| --- | --- |
| Ascorbic Acid | 92.4 |
| Microcrystalline cellulose | 4.6 |
| Hydroxypropylmethylcellulose | 2.1 |
| Moisture | 0.4 |

-continued

| Component | Percent by Weight Based on the Weight of the Dry Powder |
| --- | --- |
| Silica | 0.5 |

After the powder left the spray dryer it entered a multistage vibrating fluid bed dryer. At the same time, stearic acid was charged to first section of the fluid bed at approximately 50 lbs/hr. Air to the first section of the fluid bed should be cool enough to allow mixing before melting. The air fluidizing the second section of the fluid bed was heated to 65° C. to ensure some melting of the stearic acid. Air to the other sections was ambient.

Tablets were made on a rotary tablet press at 30 revolutions per minute. The resulting tablets had a hardness of 12 (SCU), a friability of 0.85 percent, and a disintegration time of 12.3 minutes.

EXAMPLE 2

The slurry was spray dried as in Example 1, except that silica was charged to the first section of the fluid bed along with the stearic acid (1:2 weight ratio of silica to stearic acid) at a rate of approximately 75 lbs per hour. The second section of the fluid bed was heated as in Example 1.

EXAMPLE 3

This example illustrates the use of a batch fluidized bed to mix the powder and lubricant. Into a fluid bed were charged 4540 parts of a previously spray-dried ascorbic acid powder containing approximately:

| | % |
| --- | --- |
| Ascorbic acid | 91.5 |
| Microcrystalling cellulose | 5.5 |
| Hydroxypropylmethyl cellulose | 2.5 |
| Silicon dioxide | 0.5 | and 70 parts of stearic acid powder. The bed was fluidized for 15 minutes with room temperature air to blend the stearic acid. The temperature of the fluidizing air was raised to 75° C., and sample A was taken at 30 minutes and sample B was taken at 60 minutes.

The resulting tablets made from sample A had a hardness of 11.4 (SCU), a friability of 2.2 percent, and a disintegration time of 31 minutes. The resulting tablets made from sample B had a hardness of 14.4 (SCU), a friability of 1.9 percent, and a disintegration time of 18.6 minutes.

EXAMPLE 4

This example illustrates the use of a v-blender to mix the powder and lubricant without heating.

Into a v-blender 908 parts of the same spray-dried powder as used in Example 3 was charged along with 14 parts of stearic acid. The powder was blended for 15 minutes with no heating.

Portions of the lubricated powders prepared in Examples 2 and 4 were tested to see if they were susceptible to demixing. Two 11-inch tubes 1½ inches in diameter were filled with powder from Examples 2 and 4 and were sealed at both ends. These tubes were then placed upright in a vibrating tray and vibrated for four hours. The cylinders were then divided into three equal portions—top, middle, and bottom. The top and bottom portions were then analyzed by gas chromotography using a capillary column, according to AR-14036, to determine the amount of stearic acid in each portion.

The percentage of stearic acid in the portions containing the powder from Example 2 was 1.51 percent (top) and 1.57 percent (bottom). On the other hand, the percentage of stearic acid in the portions containing the powder from Example 4 was 1.52 percent (top) and 2.24 percent (bottom).

These results indicate the powder from Example 4 demixing because there is a dffference of 0.64 percent between the amount of stearic acid in the two portions. This difference can lead to less uniformity in lubrication and can cause problems in tableting such as capping due to over lubrication, and die wall binding in the tablet press due to under lubrication. Note that the difference between the amount of stearic acid in the top and bottom portions of the powder of Example 2, which was prepared in accordance with the subject matter, was only 0.06 percent.

The embodiments of the invention in which an exclusive property or privilege is claimed are defined as follows:

1. A process for preparing a directly compressible, lubricated, water-soluble vitamin powder, which is less susceptible to demixing, and which is tablettable on a powered rotary tablet press, comprising:
   A. combining from 0.5 to 5.0 percent by weight of a powdered lubricant with an unlubricated water-soluble vitamin powder comprising:
      (a) at lease 80 percent by weight of a water-soluble vitamin; and
      (b) from about 0 to 5 percent of a binder; and
   B. mixing the powdered lubricant with the vitamin powder until a substantially uniform mixture of vitamin powder and lubricant powder is formed; and
   C. heating the mixture is a temperature sufficient to melt the lubricant, whereby the lubricant adheres to the vitamin powder; and
   D. cooling the mixture to ambient temperature whereby the lubricant is bound to the vitamin powder.

2. The process of claim 1 wherein said combining takes place in a fluidized bed dryer.

3. The process of claim 2 wherein the water-soluble vitamin is prepared by spray-drying effective amounts of an aqueous slurry of a water-soluble vitamin and a binder.

4. The process of claim 3 wherein the spray-drying is carried out in the presence of adsorbent.

5. The process of claim 4 carried out as a continuous process.

6. The process of claim 5 wherein the water-soluble vitamin is selected from the group consisting of ascorbic acid, sodium ascorbate, and calcium ascorbate.

7. The process of claim 6 wherein the amount of water-soluble vitamin, binder, adsorbent, and lubricant is such that the resulting powder will contain at least 80 percent by weight water-soluble vitamin, from 0.5 to 2.0 percent by weight adsorbent, no more than 15 percent binder, and from 0.5 to 5.0 percent byweight of lubricant.

8. The process of claim 7 wherein the lubricant is selected from the group consisting of stearic acid, magnesium stearate, and mixtures thereof.

9. The process of claim 8 wherein the adsorbent is silicon dioxide.

10. The process of claim 9 wherein the water-soluble vitamin is ascorbic acid.

11. The process of claim 2 wherein the water-soluble vitamin powder contains a water-soluble vitamin selected from the group consisting of ascorbic acid, sodium ascorbate, and calcium ascorbate.

12. The process of claim 11 wherein the lubricant is selected from the group consisting of stearic acid, magnesium stearate, and mixtures thereof.

13. The process of claim 12 wherein the temperature of the fluidized bed is at least 50° C.

* * * * *